United States Patent [19]

Ebenal, deceased et al.

[11] Patent Number: 4,526,167
[45] Date of Patent: Jul. 2, 1985

[54] SUPPORT GARMENT FOR MALES

[76] Inventors: Harry R. Ebenal, deceased, late of Daly City, Calif.; by Gladys M. Ritter, executrix, 53 Cliffside Dr., Daly City, Calif. 94015

[21] Appl. No.: 497,765

[22] Filed: May 24, 1983

[51] Int. Cl.³ .......................... A61F 5/40; A41B 9/12
[52] U.S. Cl. ........................................ 128/158; 2/403; 128/79
[58] Field of Search .................... 2/403–405; 128/158–162, 79

[56] References Cited

U.S. PATENT DOCUMENTS

| 567,343 | 9/1896 | Harden | 128/161 |
| 3,511,234 | 5/1970 | Larson | 128/159 |
| 4,014,044 | 3/1977 | Figueroa et al. | 2/2 |
| 4,173,976 | 11/1979 | Bloomquist et al. | 128/159 |
| 4,195,630 | 4/1980 | Connery et al. | 128/159 |
| 4,377,008 | 3/1983 | Jung | 128/159 |
| 4,378,010 | 3/1983 | McDonald | 128/158 X |
| 4,414,971 | 11/1983 | Chung | 128/159 |
| 4,471,772 | 9/1984 | Miller | 128/159 |

Primary Examiner—Dalton L. Truluck
Attorney, Agent, or Firm—Henderson & Sturm

[57] ABSTRACT

This invention relates to male support garments in general, and more specifically to a support garment having an interior detachable panel, that forms a vertical envelope, for supporting and immobilizing an erect male organ.

7 Claims, 2 Drawing Figures

SUPPORT GARMENT FOR MALES

BACKGROUND OF THE INVENTION

The prior art is replete with myriad male undergarment constructions as can be seen by reference to U.S. Pat. Nos.: 3,511,234; 4,014,044; 4,173,976 and 4,195,630. As diverse as these constructions are, so too are their intended purposes and functions, which include not only comfort, support and protection, but also various therapuetic or medical applications.

It should be noted however, that none of the above-mentioned devices are particularly well suited for the post-operative recovery of patients that have undergone penile prosthesis insert surgery. Obviously, in major surgery involving the male sex organ, there is quite a bit of post-operative tenderness associated therewith. In addition, particularly with respect to the penile implant surgery, one of the desired end results of this surgery, produces needs that are normally not provided for in the typical male undergarment constructions. Stated briefly, this type of surgery results in the male organ acquiring a partial to full-erection by virtue of the presence of the implant.

Due to the fact that the male organ is normally flaccid expect during periods of sexual arousal; the artificially created state of erection, not only creates unique problems attendant with the healing process, but also requires that modifications be made to the male undergarment, to support and immobilize the organ, so that the erect posture of the penis is not readily visible when the implant recipient is wearing outer garments.

Due to the foregoing facts, it became apparent that an entirely new approach to the construction of male undergarments would be required to fulfill the unique needs associated with this type of surgery. As a direct result thereof, the construction which forms the basis of this invention was developed.

SUMMARY OF THE INVENTION

An object of the present invention is to provide a totally new and unique approach to the construcion of male undergarments.

Another object of the present invention is to provide a male undergarment that will promote the healing process during the post-operative phase of penile implant surgery.

Still another object of the present invention is the construction of a male undergarment that will faciliate the change of dressings normally associated with penile implant surgery.

Yet another object of the present invention is the provision of a male support garment having a detachable envelope forming element, that will provide support and immobilization to the male organ in its partially or fully erect position.

A yet further object of the invention is the provision of a non-pinch enclosure compartment, within a male support garment, that will provide support for the male organ in an upright position.

A further object of the present invention is to provide a support garment that is specifically designed to immobilize the male organ in its upright position, so that its state of erection is not readily visible when the user is wearing outer garments.

These and other objects, advantages, and novel features of the invention will become apparent from the detailed description that follows, when considered in conjunction with the accompanying drawings.

DETAILED DESCRIPTION OF THE PREFERRED EMBODIMENT

Figure 1:
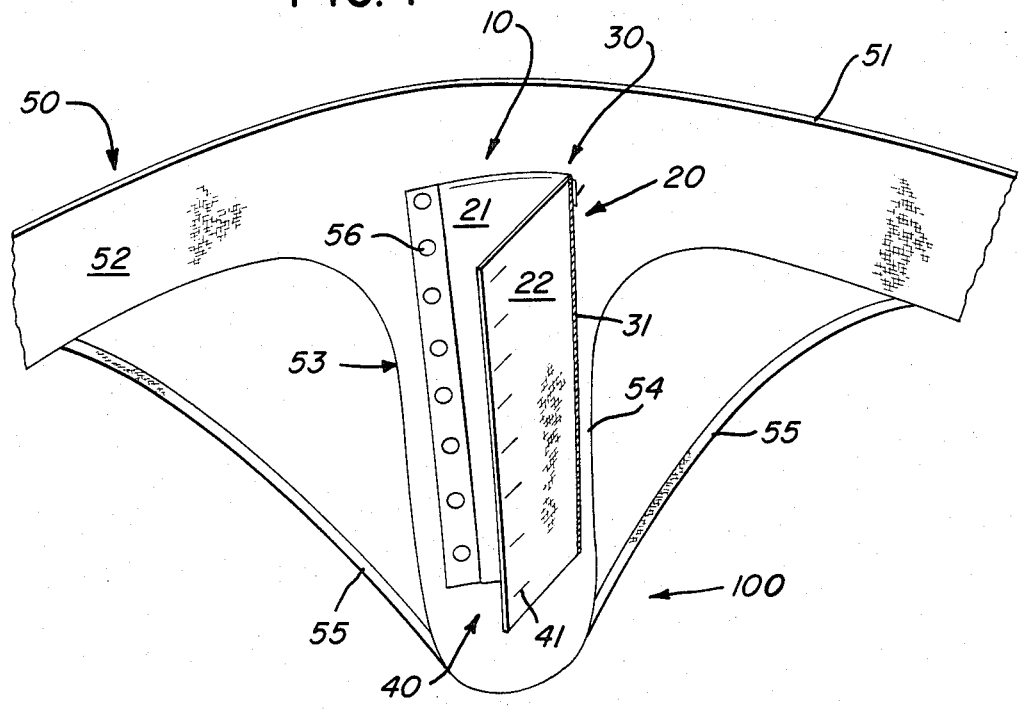
FIG. 1, depicts the improved male support garment in its open position.
Figure 2:
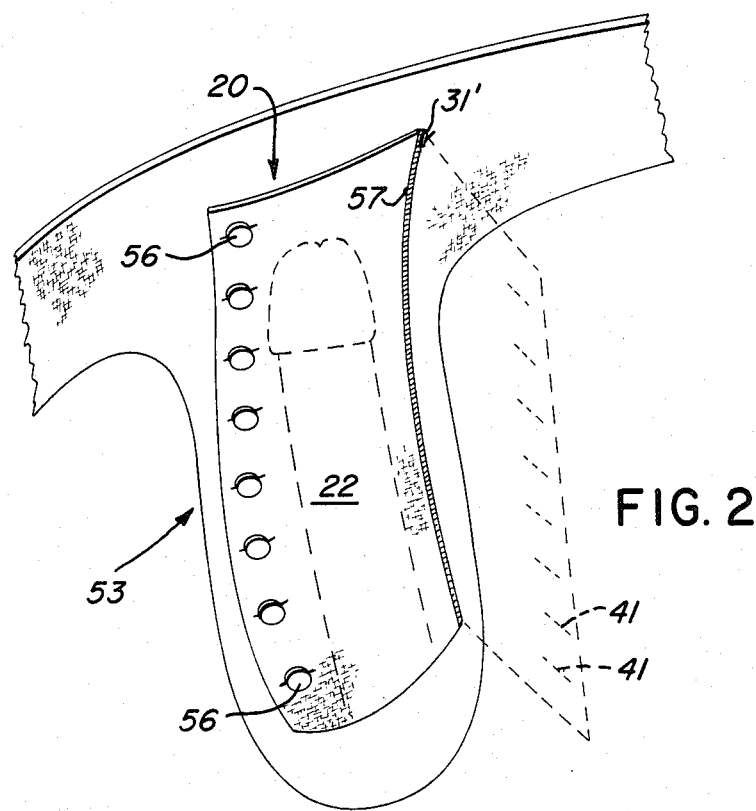
FIG. 2, depicts the improved male support garment in its closed, supporting and immobilizing position.

As can be seen by reference to FIGS. 1 and 2, a male support envelope is designated generally as 10, and is intended for incorporation into a standard male support garment designated generally as 50, to form the improved male support garment 100.

The standard male support garment 50, depicted in the drawings consists of an athletic supporter 51, comprising a wide, elastic waist band 52 having an enlarged front panel 53 in the form of a pouch 54, depending downwardly therefrom, and a plurality of thin elastic straps 55, that are connected to both the front panel 53, and the waist band 52. The thin elastic straps 55 are dimensioned to engage the users lower torso, in a well recognized manner; and maintain the pouch 54 in a position, wherein it will cover and provide support for the front of the male sex organs.

It should be appreciated at this point; that while an athletic supporter 51 has been chosen as the standard male support garment, for use in the preferred embodiment; that the male support envelope 10 can be incorporated into virtually any standard type of male undergarment, as will be explained in greater detail further on in the specification.

The male support envelope 10, is designed to be disposed on the interior surface of the front panel 53, of a standard male support garment, and comprises an elongated soft cloth envelope forming member 20, that is adapted to be detachably secured to the front panel, and encircle at least the back of the male organ to provide immobilization and support.

In one form of the preferred embodiment illustrated in FIG. 1, the envelope forming member 20, comprises two elongated pieces of soft cloth, forming a front envelope panel 21 and a rear envelope panel 22 joined together by an intermediate closure element 20 in the form of a zipper element 31. In addition, the free ends of the front and rear envelope panels are provided with fastening means 40 in the form of a plurality of button holes 41, that will cooperate with a plurality of vertically disposed buttons 56, disposed on the front panel 53 of the male support garment, to form a detachable envelope that will completely surrounded an erect penis.

In the form of the preferred embodiment, the detachable envelope forming member 20 is only connected to the standard support garment 50, by virtue of the cooperation of the buttons and buttonholes mentioned supra. The envelope forming member 20, is therefore hingedly connected to the support garment 50 to allow limited pivotal movement of the male organ in its restrained position.

It should also be noted, that while it would be simpler to fabricate the penis encircling version, without the zipper element 31, interposed between the front and rear panel members, the presence of the zipper 31 facilitates the opening of envelope to change surgical dressings, while still allowing the front and rear envelope panels to remain hingedly connected to the standard support garment. This particular construction also allows the wearer a choice, as to which of the envelope opening procedures that will employ (i.e. unbuttoning or unzippering) when attending to the call of nature; and in addition, allows the entire envelope 20 to be removed for cleaning, separate from the support In the other form of the preferred embodiment illustrated in FIG. 2, the front panel 53 of the support garment 50 is provided with a plurality of vertically disposed buttons 56, on one side and a vertically disposed zipper closure element 57 on the other side. In this version only the rear envelope panel 22 is employed, and it is provided with a plurality of buttonholes 41 and a complemenentary zipper closure element 31', for cooperation with the support garment in a well recognized manner The rear envelope panel 22 cooperates with the front support panel 53, to form a pocket that will virtually immobilize the penis in an upright position, as illustrated in FIG. 2. As in the other embodiment either the button or zipper closure member may be actuated to free the penis when required.

Both of the constructions, heretofore described, perform the same basic function, share common structural features, yet are unique from one another, while still representing as a whole, an entirely new concept in the male undergarment field. It should be appreciated that the principles employed in the preferred embodiment could be just as easily adapted to both "boxer" and "jockey" type shorts.

Having thereby described the subject matter of this invention, it should be obvious that many substitutions, modifications and alterations are possible in light of the above teachings. It is therefore to be understood that the invention as taught and described is only to be limited to the extent of the breadth and scope of the appended claims.

What is claimed is:

1. In combination with a male undergarment, comprising an elastic waist band and a front panel, an improvement comprising:
   an elongated soft cloth rear envelope forming panel, releasably secured along at least one vertical edge, to the front panel of said male undergarment, to form a vertically disposed enclosure for an erect male organ; wherein, the elongated rear envelope panel is releasably secured to the front panel of said male undergarment, along both vertical edges.

2. The improvement as in claim 1, wherein, one vertical edge of the rear envelope panel is releasably secured to the front panel of said male undergarment, by means of buttons and buttonholes.

3. The improvement as in claim 2, wherein, the other vertical edge of the rear envelope panel is releasably secured to the front panel of said male undergarment, by means of a zipper closure.

4. The improvement as in claim 1, further comprising:
   an elongated soft cloth front envelope forming panel, releasably secured along one vertical edge to the front panel of said male undergarment, such that both the front and rear envelope panels are hingedly connected to the front panel of said male undergarment.

5. The improvement as in claim 4, wherein, both the front and rear envelope panels are releasably connect at their other vertical edges, to form a penis encircling enclosure, that is hingedly attached to the front panel of said male undergarment, for the purpose of supporting an erect male organ.

6. The improvement as in claim 5, wherein, the hinged connection between the front and rear envelope panels is formed by means of buttons and buttonholes.

7. The improvement as in claim 6, wherein, the releasable connection between the said other vertical edges of said front and rear envelope panels is formed by means of a zipper closure.

* * * * *